(12) United States Patent
Choi et al.

(10) Patent No.: US 9,458,455 B2
(45) Date of Patent: Oct. 4, 2016

(54) **HIGH EFFICIENCY PLANT EXPRESSION PROMOTER FROM *CAPSICUM ANNUUM* SERINE HYDROXYMETHYL TRANSFERASE GENE AND USES THEREOF**

(75) Inventors: Do Il Choi, Seoul (KR); Sang Hyeob Lee, Daejeon (KR); Young Hee Joung, Daejeon (KR)

(73) Assignee: INDUSTRY FOUNDATION OF CHONNAM NATIONAL UNIVERSITY, Gwangju (KR)

(*) Notice: Subject to any disclaimer, the term of this patent is extended or adjusted under 35 U.S.C. 154(b) by 16 days.

(21) Appl. No.: 12/735,829

(22) Filed: Aug. 19, 2010

(65) Prior Publication Data

US 2014/0373192 A1    Dec. 18, 2014

Related U.S. Application Data

(63) Continuation of application No. PCT/KR2009/000757, filed on Feb. 18, 2009.

(30) Foreign Application Priority Data

Feb. 19, 2008 (KR) .......................... 10-2008-0014760

(51) Int. Cl.
　　*C12N 9/10*　　(2006.01)
　　*C12N 15/113*　(2010.01)
　　*C12N 15/82*　(2006.01)

(52) U.S. Cl.
　　CPC ........... *C12N 15/113* (2013.01); *C12N 9/1014* (2013.01); *C12N 15/8216* (2013.01)

(58) Field of Classification Search
　　None
　　See application file for complete search history.

(56) References Cited

U.S. PATENT DOCUMENTS 6,437,221 B1 *  8/2002  Kuntz ........................... 800/287

FOREIGN PATENT DOCUMENTS

WO    WO2009104892   *  8/2009  ............. C12N 12/82

OTHER PUBLICATIONS

Sivanandan et al. T-DNA tagging and characterization of a cryptic root-specific promoter in Arabidopsis. Biochemica Et Biophysica Acta. 2005. 1731: 202-208.*
Voll et al. The photorespiratory Arabidopsis shm1 mutant is deficient for SHM1. Plant Physiology. 2006. 140: 59-66.*

* cited by examiner

*Primary Examiner* — Shubo (Joe) Zhou
*Assistant Examiner* — Ashley K Buran
(74) *Attorney, Agent, or Firm* — The PL Law Group, PLLC (57) ABSTRACT

A high efficiency plant expression promoter from *Capsicum annuum* serine hydroxymethyl transferase gene and uses thereof. This high efficiency plant expression promoter and 5'-untranslated region (5'-UTR) from *Capsicum annuum* serine hydroxymethyl transferase gene, a high efficiency plant expression vector having the same, a plant transformed with the vector, a process for high efficiency expression of a foreign gene by using the vector and a transformed plant which expresses with high efficiency a foreign gene based on the process and seeds of the transformed plant.

7 Claims, 6 Drawing Sheets

CAAATATAAGAGAATTACTCGTAAATAAATAGCAAGTGTTTAACCATTAACTAAATCTAA
AAATTTACTTTTTCCTCTTGTCATGACATAATTTCCAACATAAGTAGTACTACTAAATTC
ATCCACTGACAAAAAGAATTCAACCACACCAAACTCTACTCATTTCCCTTGTTGTCCCCC
TATTCACCAACCTCAACACCAACTTCACCAACAAAATCAAAACAATAAAAAAATAAGTTC
TCATAAGGAGAAAGAGAAGAAGAAAATTGGGAAAAGAACAGAGTAAATAATTATTCACAT
CAAATTAATATGTATATGTTATATGGATGGATATAACTTTTTTAATGTAAATCACTTGAT
CTCTTGCTGGAAGTGCAGTCTGAGGAATATTGGGCATGTGAATTCAAACCTAATCGAATC
TATTTTAACATAAATATTAAATAATTTTGTTGAAAAAGTTATTTGACAGAATAAATATAC
GTCTTGTATTTATTCAAAATAGCGAAACTTTAAAAAATTATAATGCATTGTAAGAGTTTG
AATTTTATCTTTTGCTTTGCATCTGTTTATTTGGAGCTATATTGATTTGCTCTGTATCTA
TTCGCTCGCTTTAAAGAGCAAATTGGTACAAAATGAACAAATACAAAGTGATTCGACACA
CTAATACAAAGCAAATCATACACTAAATCACATTTTAACAAAAATAAATATCACATTTGG
TAATTAATCGCATTATTACTATAATTGATAATTATAATTTAAAGTATTGCTATTTTAAAA
ATCAATCCACTTTAAATATAGGTATCAGAGACACGGAACGAAAAAGAACAAAGGGGCAAT
ATGGACCATTAGTTTAATCCCCACCTCTTTAAATACCCCCACTCCCCTTCCTTCCCCCAT
ATCTTCAACCTTCC

*+1 AAACTTTCAACATTTCTCTTTTACCCCCTCAATTTCCCTTTCCTTCCAATTCACCCCTTC
AACTTTCTCCCCACA* ATG     (SEQ ID NO: 1)

HIGH EFFICIENCY PLANT EXPRESSION PROMOTER FROM *CAPSICUM ANNUUM* SERINE HYDROXYMETHYL TRANSFERASE GENE AND USES THEREOF

CLAIM OF PRIORITY

This application is a continuation application of my PCT International application entitled HIGH EFFICIENCY PLANT EXPRESSION PROMOTER FROM *CAPSICUM ANNUUM* SERINE HYDROXYMETHYL TRANSFERASE GENE AND USES THEREOF filed on 18 Feb. 2009 and duly assigned Serial No. PCT/KR2009/000757, which claims the priority to Korean Patent Application No. 10-2008-0014760, filed Feb. 19, 2008, the entire contents of which are incorporated herein by reference.

TECHNICAL FIELD

The present invention relates to a high efficiency plant expression promoter from *Capsicum annuum* serine hydroxymethyl transferase gene and uses thereof. More specifically, the present invention relates to a high efficiency plant expression promoter and 5'-untranslated region (5'-UTR) from *Capsicum annuum* serine hydroxymethyl transferase gene, a high efficiency plant expression vector comprising the same, a plant transformed with said vector, a process for high efficiency expression of a foreign gene by using said vector, and a transformed plant which expresses with high efficiency a foreign gene based on said process and seeds of the transformed plant.

BACKGROUND ART

Serine hydroxymethyl transferase (EC: 2.1.2.1) found in a plant is an enzyme which is involved with metabolism of glycine, serine, threonine, lysine, a cyanoamino acid, methane and the like (Oliver, D. J. Annu. Rev. Plant Physiol. Plant Mol. Biol. 1994, 45: 323-337; Igamberdiev, A. U., et al, Plant Physiol. Biochem. 1999, 37: 503-513), and it is also called glycine hydroxymethyl transferase. Five genes of serine hydroxymethyl transferase (abbreviated as SHM) have been reported for *Arabidopsis thaliana*, and EST nucleotide sequence of the gene has been also described for legumes, a tomato, a potato and the like (Shingles, R. et al. 1984, Plant Physiol. 74, 705-710; Besson, V. et al. 1995, Plant Physiol. Biochem. 33, 665-673).

Although genes for serine hydroxymethyl transferase isolated from the above-described plants have been already reported, no research has been made regarding a promoter and 5'-UTR therefor by any group in the world. Specifically, although it has been reported that an intron and UTR of polyubiquitin gene have an effect on the polyubiquitin gene in corn or gladiolus and introns for several other genes can increase expression of the gene itself (Wang J and Oard J H, 2003, Plant Cell Rep 22:129-134; Norris S R et al, 1993, Plant Mol Biol 21:895-906), there is no research regarding whether UTR of serine hydroxymethyl transferase gene has an effect on expression regulation of the gene itself.

Recently, various studies have been made to produce commercially useful materials based on a genetic engineering technology, i.e., with introduction of a foreign gene in a plant. When a commercially useful foreign gene is desired to be expressed in a transformed plant, a promoter that is related to expression of the gene is also required. For this, a promoter from cauliflower mosaic virus (CaMV35S), which is expressed in any type of a tissue of a plant, has been widely used. However, there is a problem in that, since an expression amount of a foreign gene is low, the expression is less than 0.1% of the entire expression amount of water-soluble proteins. Thus, a strong promoter which is capable of increasing expression of a foreign gene in a transformed plant is urgently required. Further, in order to achieve temporary but large-scale expression of a foreign gene in a plant tissue based on a transient method, a new strong plant promoter is also very much required.

In Korean Patent Reg. No. 0604186, a nucleotide sequence of a promoter for high efficiency expression of a sweet potato (*Ipomoea batatas* L.) storage roots, a vector for transient and high efficiency plant expression comprising the promoter sequence, and a method for transient expression in storage roots of a plant by using the expression vector are disclosed. In Korean Patent Reg. No. 0574563, a high efficiency expression promoter from *Arabidopsis thaliana* and a vector comprising the promoter for high efficiency expression in plant are disclosed. However, these promoters are different from the promoter of the present invention.

DISCLOSURE OF INVENTION

Technical Problem

The present invention, which is devised in view of the necessities described in the above, is based on the finding that the expression of serine hydroxymethyl transferase gene is higher than expression of other genes according to microarray analysis of *Capsicum annuum* (a species of hot pepper). According to the present invention, the promoter and 5'-UTR of said serine hydroxymethyl transferase gene are cloned and inserted to a binary vector, which is then introduced to a model plant, *Arabidopsis thaliana*. As a result, the gene expression in *Arabidopsis thaliana* was almost five times higher than CaMV35S promoter from cauliflower mosaic virus. Further, it was found that the transient expression was enhanced almost 30 times in a callus tissue of a rose and a gladiolus and a leaf tissue of *Capsicum annuum*. Consequently, the present invention was completed.

Technical Solution

In order to solve the problems described in the above, the present invention provides a high efficiency plant expression promoter or 5'-UTR for expression enhancement that are derived from *Capsicum annuum* serine hydroxymethyl transferase gene.

Further, the present invention provides a high efficiency plant expression promoter vector which comprises the above described high efficiency plant expression promoter and/or 5'-UTR for expression enhancement, and a plant which is transformed with the expression vector.

Further, the present invention provides a process for high efficiency expression of a foreign gene by using the above described high efficiency expression promoter and/or 5'-UTR for expression enhancement based on transformation and a transient method, when a useful substance is desired to be produced in large scale in a plant.

Still further, the present invention provides a transformed plant prepared based on said process and seeds of the transformed plant, wherein said transformed plant expresses a foreign gene with high efficiency.

Advantageous Effects

According to the present invention, with expression of a foreign gene in a plant using high efficiency expression promoter and/or 5'-UTR derived from serine hydroxymethyl transferase gene of *Capsicum annuum* (hereinafter, abbreviated as CaSHM), a novel promoter which can enhance expression of a foreign gene about 5 to 30 times compared to conventionally used CaMV 35S promoter is found. It is also found that, the promoter of the present invention has higher activity in dicot plants, monocot plants, and trees compared to CaMV 35S promoter.

BRIEF DESCRIPTION OF DRAWINGS

FIG. 4-A shows the results of GUS staining of *Arabidopsis thaliana* that have been transformed with pCAM-SHM (SHM), pCAMBIA1391Z (-P), or pCAMBIA 1301 (35S) that are shown in FIG. 3, respectively. FIG. 4-B represents GUS enzymatic activity in transformed *Arabidopsis thaliana*.

FIG. 5-A shows the result of GUS staining of callus tissues of a rose or a gladiolus wherein pUC-SHM (SHM), pUC-GUS (-35S) or pUC-35SGUS (35S) of FIG. 3 was subjected to transient expression in a plant based on a particle bombardment. FIG. 5-B represents GUS enzymatic activity based on transient method in callus tissues and leaves.

MODE FOR THE INVENTION

Figure 2:
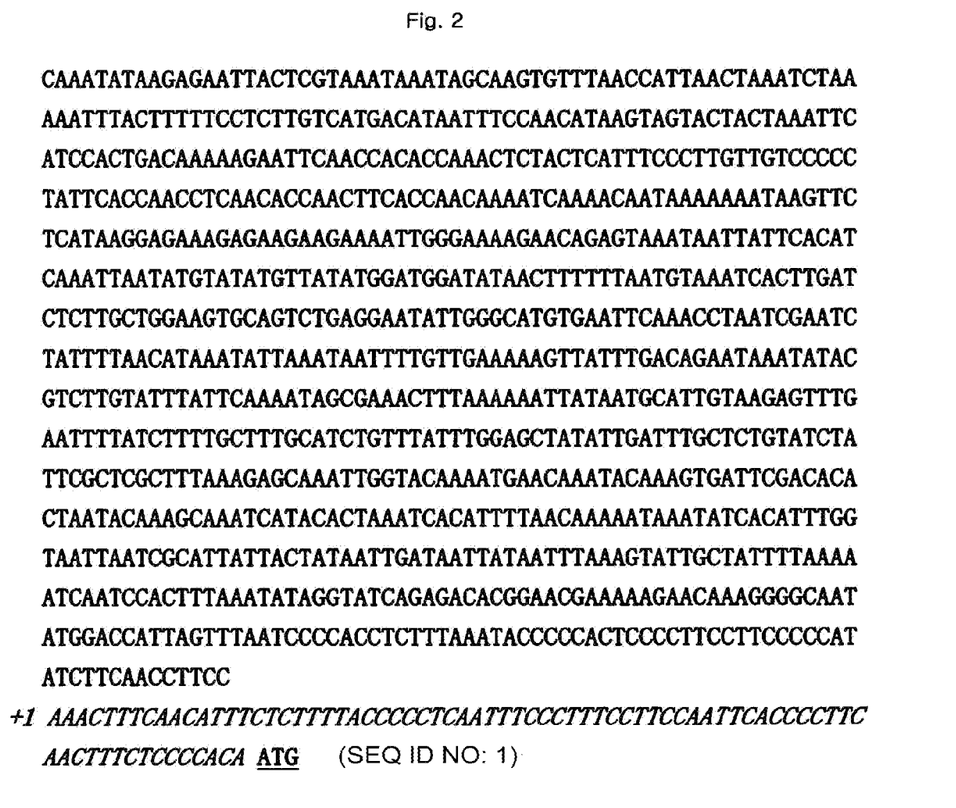
FIG. 2 shows the nucleotide sequence of the promoter and 5'-UTR of CaSHM gene of the present invention.

In order to achieve the purpose of the invention as described in the above, the present invention provides a high efficiency plant expression promoter which comprises a nucleotide sequence of nucleotide base number 1 to number 914 (i.e., −914 to −1, starting from the transcription initiation site) of the sequence shown in FIG. 2 (SEQ ID NO: 1).

The high efficiency expression promoter of the present invention as described in the above can significantly enhance expression of a gene in a transformed plant, compared to CaMV35S promoter from cauliflower mosaic virus that is conventionally used in general.

In order to achieve the purpose of the invention as described in the above, the present invention also provides 5'-UTR for enhancing expression in a plant, wherein the 5'-UTR comprises the nucleotide sequence of nucleotide base number 915 to number 989 (i.e., +1 to +75, starting from the transcription initiation site) of the sequence shown in FIG. 2 (SEQ ID NO: 1). Still further, according to one embodiment of the present invention, a plant expression vector in which part of 5'-UTR described above is comprised is constructed. Specifically, a plant expression vector comprising a nucleotide sequence including from base number +1 to base number +36, numbered from the transcription initiation site of SEQ ID NO: 1, was constructed. Thus, the 5'-UTR for enhancing the expression in a plant of the present invention includes not only the nucleotide sequence from base number +1 to base number +36 numbered from the transcription initiation site of SEQ ID NO: 1 but also the nucleotide sequence from base number +1 to base number +75 numbered from the transcription initiation site of SEQ ID NO: 1.

5'-UTR for enhancing the expression in a plant of the present invention can significantly enhance the expression of a target gene by aiding transcription initiation of a gene that is introduced in a plant, by increasing stability of transcribed mRNA, or by improving the translation efficiency of a gene.

In addition, a sequence variant of the above described promoter or 5'-UTR is also included in the scope of the present invention. The term "variant" means a nucleotide sequence which may have a different nucleotide sequence but has a similar functional characteristic compared to the nucleotide sequence of SEQ ID NO: 1. Specifically, the above described promoter sequence and 5'-UTR sequence may have a nucleotide sequence which has sequence homology of at least 70%, preferably at least 80%, more preferably at least 90%, still more preferably at least 95% compared to the nucleotide sequence of SEQ ID NO: 1.

Said "sequence homology %" for a certain polynucleotide is identified by comparing a comparative region with two sequences that are optimally aligned. In this regard, a part of the polynucleotide in comparative region may comprise an addition or a deletion (i.e., a gap) compared to a reference sequence (without any addition or deletion) relative to the optimized alignment of the two sequences.

In order to achieve another purpose of the present invention, the present invention provides a high efficiency plant expression vector which comprises a high efficiency plant expression promoter and/or 5'-UTR for expression enhancement.

The high efficiency plant expression vector of the present invention may comprise only the promoter of the present invention, or 5'-UTR of the present invention can be used in combination with other general plant expression promoter such as CaMV 35S promoter. Preferably, however, having both the promoter and the 5'-UTR of the present invention is advantageous for obtaining high efficiency expression of a foreign gene introduced in a plant.

The high efficiency plant expression vector of the present invention may be used as a transient expression vector which can transiently express a foreign gene in a plant or as a plant expression vector which can permanently express a foreign gene in a plant.

A binary vector which can be used for the present invention can be any binary vector comprising RB (right border) and LB (left border) of T-DNA which can transform a plant when it is present with Ti plasmid of *A. tumefaciens*. Preferably, pBI101 (Cat 6018-1, Clontech, USA), pBIN19 (Genbank Deposit No. U09365), pBI121, pCAMBIA and the like, which are often used by a skilled person in the pertinent art, are used.

Figure 3:
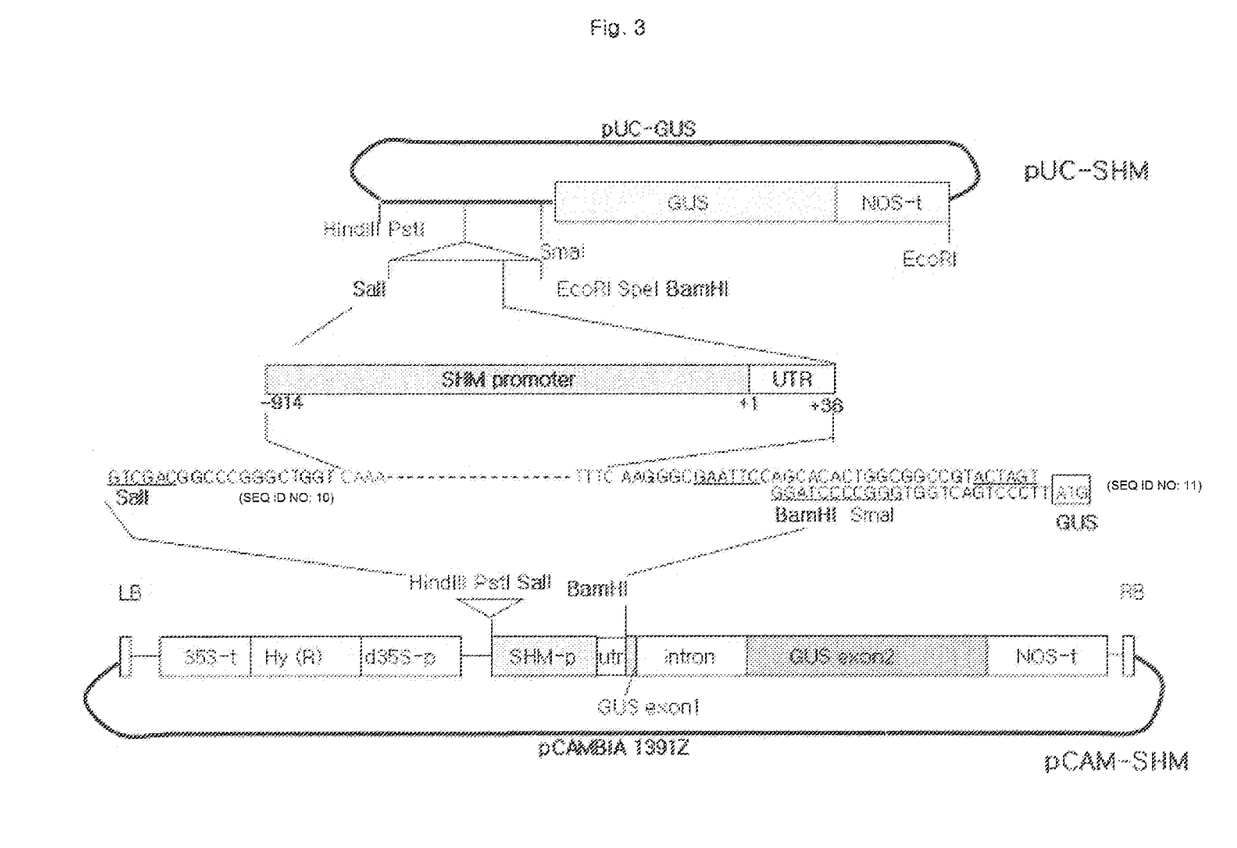
FIG. 3 is a schematic diagram showing plant expression vectors pCAM-SHM and pUC-SHM that are produced by inserting the promoter and part of 5'-UTR of CaSHM gene to a reporter gene, β-glucuronidase (hereinafter, abbreviated as GUS).

According to one embodiment of the present invention, a high efficiency plant expression vector can be pUC-SHM or pCAM-SHM depicted in FIG. 3, but not limited thereto. pUC-SHM vector in which GUS reporter gene as one example of a foreign gene is inserted in pUC18 vector and the promoter and 5'-UTR are placed in front of the gene (see, FIG. 3) can be used for plant transformation based on particle bombardment and also for transient expression. In addition, the promoter and 5'-UTR of the present invention are inserted into a binary vector (pCAMBIA 1391Z) for analyzing a promoter to give pCAM-SHM (FIG. 3) wherein GUS gene is comprised. Then, the vector is used for plant transformation using *Agrobacterium*. It would be obvious for a skilled person in the art that said GUS reporter gene can be replaced with other target foreign gene.

The term "vector" is used herein to refer DNA fragment (s) and nucleotide molecules that are delivered to a cell. Vector can be used for the replication of DNA and be independently reproduced in a host cell. The terms "delivery system" and "vector" are often interchangeably used. The term "expression vector" means a recombinant DNA molecule comprising a desired coding sequence and other appropriate nucleotide sequences that are essential for the expression of the operatively-linked coding sequence in a specific host organism. A promoter, an enhancer, a termination signal and a polyadenylation signal that can be used for an eukaryotic cell are all publicly well known.

A preferred example of plant expression vector is Ti-plasmid vector which can transfer a part of itself, i.e., so-called T-region, to a plant cell when the vector is present in an appropriate host such as *Agrobacterium tumefaciens*. Other types of Ti-plasmid vector (see, EP 0 116 718 B1) are currently used for transferring a hybrid gene to protoplasts that can produce a new plant by appropriately inserting a plant cell or hybrid DNA to a plant genome. Especially preferred form of Ti-plasmid vector is a so-called binary vector which has been disclosed in EP 0 120 516 B1 and U.S. Pat. No. 4,940,838. Other appropriate vectors that can be used for introducing the DNA of the present invention to a host plant can be selected from a double-stranded plant virus (e.g., CaMV), a single-stranded plant virus, and a viral vector which can be originated from Gemini virus, etc., for example a non-complete plant viral vector. Use of said vector can be especially advantageous when a plant host cannot be appropriately transformed.

Expression vector preferably comprises at least one selection marker. Said selection marker is a nucleotide sequence having a property which allows a selection based on a common chemical method. Any kind of gene that can be used for the differentiation of transformed cells from non-transformed cells can be a selection marker. Example includes, a gene resistant to herbicide such as glyphosate and phosphinotricin, and a gene resistant to antibiotics such as kanamycin, G418, bleomycin, hygromycin, and chloramphenicol, but not limited thereto.

With respect to a terminator for a plant expression vector of one embodiment of the present invention, any typical terminator can be used. Examples thereof include nopaline synthase (NOS), rice α-amylase RAmyl A terminator, phaseoline terminator, a terminator for octopine gene of *Agrobacterium tumefaciens* and the like, but not limited thereto.

In order to achieve another purpose of the present invention, the present invention provides *E. coli* or *Agrobacterium tumefaciens* that is transformed with the high efficiency plant expression vector of the present invention.

In order to achieve another purpose of the present invention, the present invention provides a plant that is transformed with the high efficiency plant expression vector of the present invention and seeds of the plant.

The high efficiency plant expression vector of the present invention can be used for transformation of any plant including a dicot and a monocot plant. In the present invention, transformation was carried out using *Arabidopsis*. The plant according to one embodiment of the present invention can be a dicot plant such as potato, *Arabidopsis*, eggplant, tobacco, pepper, tomato, burdock, crown daisy, lettuce, Chinese bellflower, chard, spinach, sweet potato, celery, carrot, coriander, parsley, Chinese cabbage, cabbage, leaf mustard, watermelon, melon, cucumber, zucchini, gourd, strawberry, soy bean, mung bean, kidney bean, sweet pea and the like.

Promoter activity in a monocot plant or in a tree was confirmed by carrying out transient expression of a foreign gene in a callus tissue based on particle bombardment method.

Transformation of a plant means any method which can transfer DNA to a plant. Such transformation is not necessarily required to have a period for regeneration and/or tissue culture. Transformation of a plant is now generally carried out not only for a dicot plant but also for a monocot plant. In principle, any method for transformation can be used for introducing a heterologous DNA of the present invention to a progenitor cell. Transformation can be carried out according to any method selected from a calcium/polyethylene glycol method for protoplasts (Krens, F. A. et al., 1982, Nature 296, 72-74; Negrutiu I. et al., June 1987, Plant Mol. Biol. 8, 363-373), an electroporation method for protoplasts (Shillito R. D. et al., 1985 Bio/Technol. 3, 1099-1102), a microscopic injection method for plant components (Crossway A. et al., 1986, Mol. Gen. Genet. 202, 179-185), a particle bombardment method for various plant components (DNA or RNA-coated) (Klein T. M. et al., 1987, Nature 327, 70), or a (non-complete) viral infection method in *Agrobacterium tumefaciens* mediated gene transfer by plant invasion or transformation of fully ripened pollen or microspore (EP 0 301 316), etc. According to the present method, *Agrobacterium* mediated DNA transfer is preferred. In particular, so-called binary vector technique as disclosed in EP A 120 516 and U.S. Pat. No. 4,940,838 can be preferably adopted for the present invention.

The plant cell that is used for the plant transformation according to the present invention can be any plant cell. The plant cell can be a cultured cell, a cultured tissue, a cultured organ, or a whole plant, preferably a cultured cell, a cultured tissue or a cultured organ, and more preferably any form of a cultured cell.

The plant tissue includes either differentiated or undifferentiated plant tissue, including root, stem, leaf, pollen, seed, cancerous tissue and cell lines having various shape that are used for culture, i.e., single cell, protoplast, bud and callus tissue, but not limited thereto. Plant tissue can be in planta or in a state of organ culture, tissue culture or cell culture.

In order to achieve another purpose of the invention, the present invention provides a process for high efficiency expression of a foreign gene in a plant comprising steps of:

carrying out recombination of a foreign gene in the high efficiency plant expression vector of the present invention, and transforming a plant with the recombinant plant expression vector.

Any gene which is desired to be expressed in a mass amount can be employed as a foreign gene. It is placed in the downstream region of the promoter and 5'-UTR in the high efficiency plant expression vector of the present invention, and if necessary, it can be expressed as being fused with a reporter gene. Transformation of a plant with the recombinant plant expression vector of the present invention can be carried out according to the process as described in the above.

In order to achieve yet another purpose of the invention, the present invention provides a transformed plant that is produced according to the process described above wherein a foreign gene is expressed with high efficiency, and seeds of the plant. The transformed plant can express a foreign gene with high efficiency with an aid of a high efficiency expression promoter and 5'-UTR.

The present invention will now be described in greater detail with reference to the following examples. However, it is only to specifically exemplify the present invention and in no case the scope of the present invention is limited by these examples.

EXAMPLES

Example 1

Obtainment of a Promoter and 5'-UTR from CaSHM Gene and Their Sequencing

As a result of microarray analysis of *Capsicum annuum*, a serine hydroxymethyl transferase having high expression ratio was selected and from the EST library of *Capsicum annuum*, nucleotide sequence of the transferase gene and part of 5'-UTR were identified (KS00079B11). To securely obtain the promoter and 5'-UTR for said gene, SHM-specific primers were produced based on EST nucleotide sequence of KS09079B 11. i.e., SHMGS 1: GTT GAA GGG GTG AAT TGG AAG GAA AGG (SEQ ID NO: 2) and SHMGS2: GAA ATT GAG GGG GTA AAA GAG AAA TGT T(SEQ ID NO: 3). Genomic DNA was extracted from young leaves of *Capsicum annuum*, and digested with restriction enzymes of Dra I, Eco RV, Pvu II, and Stu I based on a method provided by Universal Genome Walker Kit (Clontech). Then, after ligation with an adapter comprised in the kit, 4 different kinds of libraries were constructed. Based on these, first polymerase chain reaction (hereinafter, referred to as PCR) was carried out using GWAP1 adapter primer (GTA ATA CGA CTC ACT ATA GGG C (SEQ ID NO: 4)) and SHMGS1 primer, followed by dilution of 50 times. Then, by using GWAP2 adapter primer (ACT ATA GGG CAC GCG TGG T (SEQ ID NO: 5)) and SHMGS2 primer, second PCR was carried out (see, FIG. 1). About 1 kb DNA fragment which had been amplified by PCR was cloned in pCR-TOPO TA vector (Invitrogen, USA) and its nucleotide sequence was analyzed (FIG. 2). In the figure, italicized nucleotide sequence corresponds to 5'-untranslated region of the gene. In addition, initiation codon for protein synthesis, i.e., ATG, is written in bold letter and a site for transcription initiation is designated as +1.

Example 2

Identification of Transcription Initiation Site for CaSHM

In order to study the activity of the promoter site of CaSHM, exact initiation site of gene transcription should be identified first. As such, based on cRACE (circular first-strand cDNA-mediated rapid amplification of cDNA ends; Nucleic Acid Research 23: 3796-3797, 1995), transcription initiation site for CaSHM gene was determined first. Specifically, total RNA was isolated from young leaves of *Capsicum annuum*, and by using a reverse transcriptase (Super Script™ II RT, GIBCO BRL), a cDNA pool was established and then having it as a template and using a gene-specific primer ((CaSHMAS1: 5'-AGA GGT TCG TTA CCC CAA ACG-3' (SEQ ID NO: 6) and CaSHMAS2: 5'-CCA AAC GGT GAC GGG ATC CAT-3' (SEQ ID NO: 7)) and an adapter primer of cDNA library ((RTAP1; 5'-CCA TCC TAA TAC GAC TCA CTA TAG GGC-3' (SEQ ID NO: 8) and RTAP2; 5'-ACT CAC TAT AGG GCT CGA GCG GC-3' (SEQ ID NO: 9)) PCR was carried out. As a result, it was confirmed that nucleotide base number 75 from the translation initiation codon (ATG) was identified as a transcription initiation site. In FIG. 2, it is marked with +1 (FIG. 2).

Example 3

Figure 1:
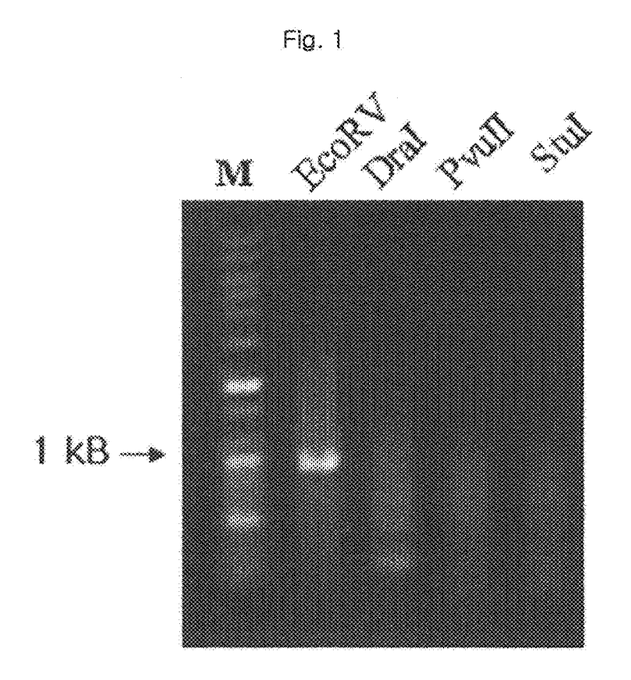
FIG. 1 shows the PCR result to isolate a promoter for serine hydroxymethyl transferase gene of *Capsicum annuum* from genome of *Capsicum annuum* based on Genome Walking method.

Construction of a Plant Expression Vector by using the Promoter and 5'-UTR of CaSHM Gene The promoter and UTR fragment of CaSHM gene, which had been obtained as shown in FIG. 1 and then inserted to pCR-TOPO TA vector, were digested with the restriction enzymes of SalI and BamHI. Resulting fragments were recovered and cloned in pUC18 vector (pUC-GUS) comprising GUS reporter gene to construct pUC-SHM (FIG. 3). Also, CaMV35S promoter derived from pBI121 was cloned in pUC-GUS to construct pUC-35SGUS vector. Then, in accordance with a transient expression method, activity of the promoters was compared to each other. The fragment that had been recovered from the treatment of pCR-TOPO vector with SalI/BamHI was cloned in pCAMBIA 1391Z, and the resulting pCAM-SHM vector was used for plant transformation using *Agrobacteria*.

Example 4

Transformation of *Arabidopsis thaliana* Using the Plant Expression Vector of the Present Invention (pCAM-SHM)

*Agrobacterium tumefaciens* C58C1 was transformed with the plant expression vectors as prepared in the above, i.e., pCAM-SHM, pCAMBIA 1301, and pCAMBIA 1391Z, respectively, based on a freeze-thaw method (An, G. 1987, Methods in Enzymology, 153: 292-293). Each of the transformed *Agrobacteria* was cultured at 28° C. for two days under shaking. Then, using vacuum infiltration (Bechtold and Pelletier 1998, Methods Mol Biol 82:259-266), about five-week-old *Arabidopsis thaliana* (ecotype, Columbia) was transformed with them.

Example 5

Histochemical Staining and Enzymatic Analysis of Transformed *Arabidopsis thaliana*

Figure 4:
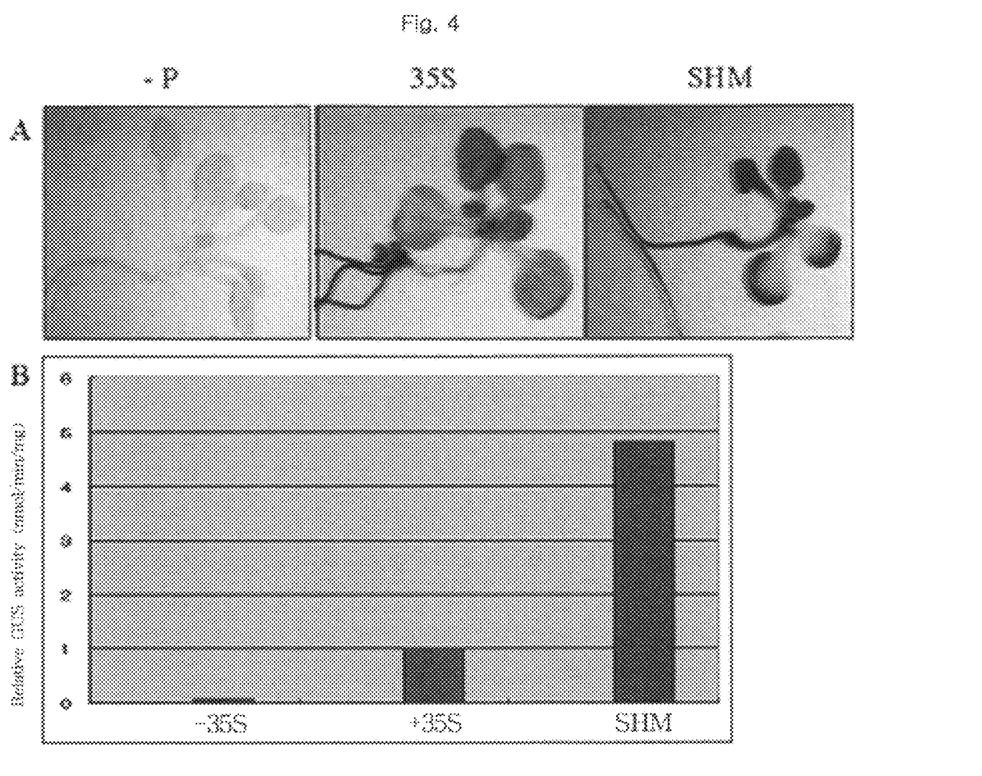

After harvesting seeds from the transformed *Arabidopsis thaliana* as produced in the above, they were added in MS culture medium comprising hygromycin (30 mg/L) and then a transformant having resistance to antibiotics was selected. From thus-selected transformed plants, GUS activity was determined based on a histochemical staining method and an enzymatic method. In order to stain whole tissue of each of the transformed plants, plant tissues were reacted in a solution comprising 1 mM X-glu (5-bromo-4-chloro-β-indolyl-β-glucuronide), 100 mM sodium phosphate (pH 7.0), 10 mM EDTA, 0.5 mM potassium ferricyanide, 0.5 mM potassium ferrocyanide and 0.1% Triton X-100 at 37° C. for 12 hours. Then, by using 100% ethanol, chlorophylls were removed. In FIG. 4-A, SHM represents *Arabidopsis thaliana* transformed with pCAM-SHM, -P represents a control group wherein *Arabidopsis thaliana* was transformed with pCAMBIA 1391Z comprising GUS gene but no promoter, and 35S represents *Arabidopsis thaliana* which was transformed with pCAMBIA 1301 comprising GUS gene and CaMV35S promoter. As a result, it was found that, GUS activity is stronger in *Arabidopsis thaliana* that has been transformed with pCAM-SHM, compared to the transformation with CaMV35S.

Further, for quantitative analysis of GUS activity, each tissue of a transformed plant was ground in a solution comprising 50 mM sodium phosphate (pH 7.0), 10 mM EDTA, 0.1% Triton X-100, 0.1% sodium lauroylsarcosine and 10 mM β-mercaptoethanol, followed by centrifuge at 16,000×g to obtain a supernatant, according to the method described by Jefferson et. al. (EMBO J. 6: 3901-3907, 1987). Thus obtained supernatant was admixed with 1 mM MUG (4-methylumbelliferyl glucuronide) and reacted at 37° C. The reaction was terminated by addition of 0.2 M $Na_2CO_3$. Fluorescence of the solution obtained after the termination of the reaction was measured by using a fluoromoter (excitation wavelength 360 nm and emission wavelength 460 nm). The measured value was then compared against a standard curve that is constructed by using MUG standard solution to obtain GUS activity. Results of the obtained GUS activity are shown in FIG. 4-B. The GUS activities shown in the figure are obtained from ten separate transformants ($T_1$ plant) that had been prepared for each construct. As a result, it was found that the promoter for CaSHM gene of the present invention shows GUS expression profile that is about 5 times stronger than that of CaMV35S.

Example 6

Figure 5:
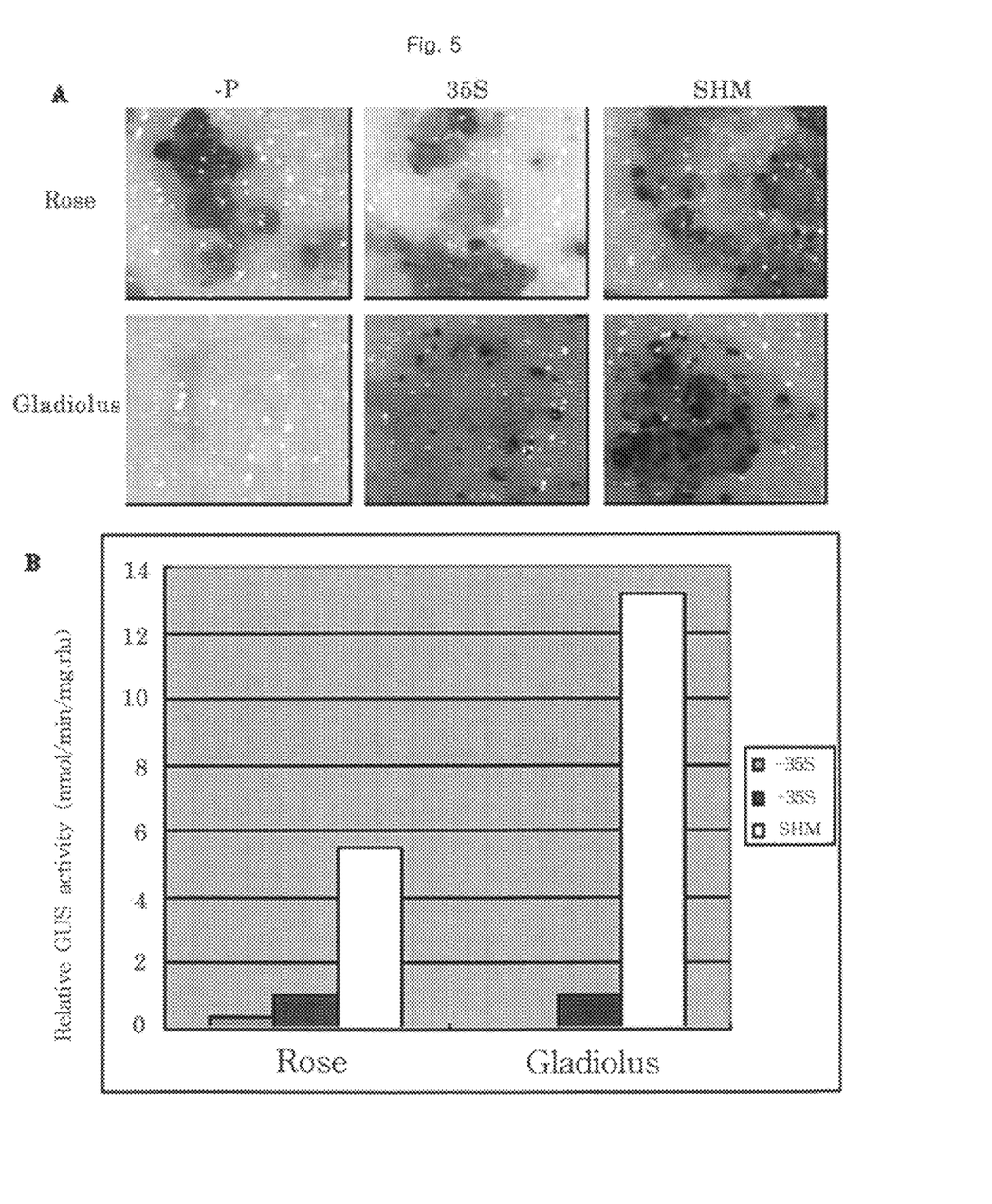

Analysis of CaSHM Promoter Activity in a Tree and a Monocot Plant by Using a Transient Analysis DNA for each of pUC-SHM (SHM), pUC-35SGUS (35S), and pUC-GUS (-P) was isolated according to the method by Sanford et al. (1993, Methods Enzymol 217:483-510), and then coated with gold particles having 10 □m size. Thereafter, by using PDS-1000 He System, the coated particles were bombarded on a plant tissue. Each of said vectors was admixed with the same amount of pD0432 vector including luciferase gene, and with co-bombardment GUS activity was quantified. The bombarded plant tissues were cultured at 25° C. for about two days under dark condition, and then tissues were ground for GUS activity measurement. Compared to the GUS activity that is expressed by CaMV35S, GUS activity in rose was increased about 5 times by CaSHM promoter. Further, GUS activity in gladiolus was also increased about 13 times by CaSHM promoter (FIG. 5).

Example 7

Analysis of Effect by 5'-UTR of CaSHM Gene on Gene Expression

Figure 6:
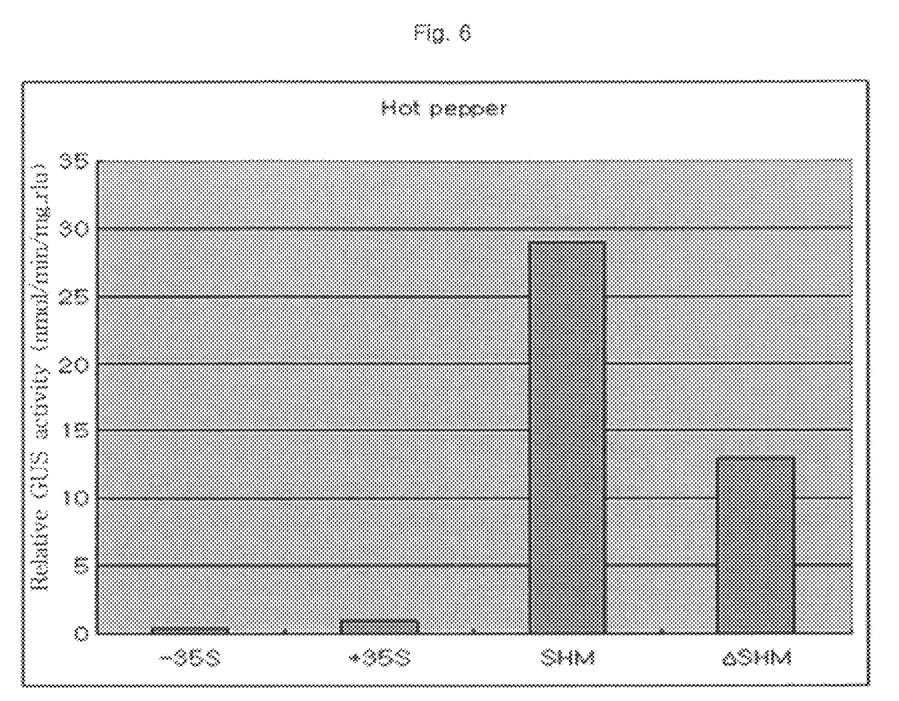
FIG. 6 shows the effect of 5'-UTR of CaSHM gene on the activity on the SHM promoter.

With cloning of a promoter lacking UTR region of CaSHM, pUC-ASHM vector was constructed. By using this vector, an effect by 5'-UTR of CaSHM on the activity of SHM promoter was determined. Specifically, with observation of transient expression that had been achieved by particle bombardment on leaves of *Capsicum annuum*, it was found that, with the presence of UTR, GUS activity was almost 30 times stronger than CaMV35S. Further, even without UTR, GUS activity was almost 15 times stronger than CaMV35S. It is obvious that there was almost two-fold increase in gene expression by the presence of UTR (FIG. 6).

The invention claimed is:

1. A construct comprising a plant expression promoter comprising nucleotides 1 to 914 of SEQ ID NO: 1 operably linked to a heterologous sequence to be expressed.

2. A construct comprising a 5'-UTR comprising nucleotides 915 to 989 of SEQ ID NO: 1 operably linked to a promoter and a heterologous sequence to be expressed.

3. A plant expression vector comprising the construct of claim 1, a sequence comprising nucleotides 915 to 989 of SEQ ID NO: 1 operably linked to a promoter and a heterologous sequence to be expressed, or SEQ ID NO: 1 operably linked to a heterologous sequence to be expressed.

4. An *Agrobacterium tumefaciens* transformed with the plant expression vector of claim 3.

5. A plant transformed with the plant expression vector of claim 3.

6. A method for expression of a transcribable nucleotide sequence in a plant comprising:
transforming a plant with the plant expression vector of claim 3.

7. A transformed seed from the plant of claim 5, wherein the seed comprises the plant expression vector.

* * * * *

UNITED STATES PATENT AND TRADEMARK OFFICE
CERTIFICATE OF CORRECTION

PATENT NO. : 9,458,455 B2
APPLICATION NO. : 12/735829
DATED : October 4, 2016
INVENTOR(S) : Young Hee Joung, Do Il Choi and Sang Hyeob Lee It is certified that error appears in the above-identified patent and that said Letters Patent is hereby corrected as shown below:

On the Title Page

Item (12), "Choi, et al." should read -- Joung, et al. --

Item (72), The order of the inventor's names read:
"Do Il Choi, Seoul, (KR)
Sang Hyeob Lee, Daejeon, (KR)
Young Hee Joung, Daejeon, (KR)"

The order of the inventor's names should read:
-- Young Hee Joung, Daejeon, (KR)
Do Il Choi, Seoul, (KR)
Sang Hyeob Lee, Daejeon, (KR) --

Signed and Sealed this
Twenty-seventh Day of December, 2016

Michelle K. Lee
*Director of the United States Patent and Trademark Office*

SEQUENCE LISTING

```
<160> NUMBER OF SEQ ID NOS: 11

<210> SEQ ID NO 1
<211> LENGTH: 992
<212> TYPE: DNA
<213> ORGANISM: Capsicum annuum

<400> SEQUENCE: 1
caaatataag agaattactc gtaaataaat agcaagtgtt taaccattaa ctaaatctaa      60
aaatttactt tttcctcttg tcatgacata atttccaaca taagtagtac tactaaattc     120
atccactgac aaaaagaatt caaccacacc aaactctact catttccctt gttgtccccc     180
tattcaccaa cctcaacacc aacttcacca acaaaatcaa aacaataaaa aaataagttc     240
tcataaggag aaagagaaga agaaaattgg gaaaagaaca gagtaaataa ttattcacat     300
caaattaata tgtatatgtt atatggatgg atataaacttt tttaatgtaa atcacttgat    360
ctcttgctgg aagtgcagtc tgaggaatat tgggcatgtg aattcaaacc taatcgaatc     420
tattttaaca taaatattaa ataattttgt tgaaaaagtt atttgacaga ataaatatac     480
gtcttgtatt tattcaaaat agcgaaactt taaaaaatta taatgcattg taagagtttg     540
aattttatct tttgctttgc atctgtttat ttggagctat attgatttgc tctgtatcta     600
ttcgctcgct ttaaagagca aattggtaca aaatgaacaa atacaaagtg attcgacaca     660
ctaatacaaa gcaaatcata cactaaatca cattttaaca aaaataaata tcacatttgg    720
taattaatcg cattattact ataattgata attataattt aaagtattgc tattttaaaa    780
atcaatccac tttaaatata ggtatcagag acacggaacg aaaaagaaca aagggcaat      840
```

-continued

```
atggaccatt agtttaatcc ccacctcttt aaatacccccc actccccttc cttcccccat    900
atcttcaacc ttccaaactt tcaacatttc tcttttaccc cctcaatttc cctttccttc    960
caattcaccc cttcaacttt ctccccacaa tg                                  992
```

<210> SEQ ID NO 2
<211> LENGTH: 27
<212> TYPE: DNA
<213> ORGANISM: Artificial Sequence
<220> FEATURE:
<223> OTHER INFORMATION: SHMGS1 primer

<400> SEQUENCE: 2
gttgaagggg tgaattggaa ggaaagg                                        27

<210> SEQ ID NO 3
<211> LENGTH: 28
<212> TYPE: DNA
<213> ORGANISM: Artificial Sequence
<220> FEATURE:
<223> OTHER INFORMATION: SHMGS2 primer

<400> SEQUENCE: 3
gaaattgagg gggtaaaaga gaaatgtt                                       28

<210> SEQ ID NO 4
<211> LENGTH: 22
<212> TYPE: DNA
<213> ORGANISM: Artificial Sequence
<220> FEATURE:
<223> OTHER INFORMATION: GWAP1 adaptor primer

<400> SEQUENCE: 4
gtaatacgac tcactatagg gc                                             22

<210> SEQ ID NO 5
<211> LENGTH: 19
<212> TYPE: DNA
<213> ORGANISM: Artificial Sequence
<220> FEATURE:
<223> OTHER INFORMATION: GWAP2 adaptor primer

<400> SEQUENCE: 5
actatagggc acgcgtggt                                                 19

<210> SEQ ID NO 6
<211> LENGTH: 21
<212> TYPE: DNA
<213> ORGANISM: Artificial Sequence
<220> FEATURE:
<223> OTHER INFORMATION: CaSHMAS1 primer

<400> SEQUENCE: 6
agaggttcgt taccccaaac g                                              21

<210> SEQ ID NO 7
<211> LENGTH: 21
<212> TYPE: DNA
<213> ORGANISM: Artificial Sequence
<220> FEATURE:
<223> OTHER INFORMATION: CaSHMAS2 primer

<400> SEQUENCE: 7
ccaaacggtg acgggatcca t                                              21

-continued

```
<210> SEQ ID NO 8
<211> LENGTH: 27
<212> TYPE: DNA
<213> ORGANISM: Artificial Sequence
<220> FEATURE:
<223> OTHER INFORMATION: RTAP1 primer

<400> SEQUENCE: 8
ccatcctaat acgactcact atagggc                                         27

<210> SEQ ID NO 9
<211> LENGTH: 23
<212> TYPE: DNA
<213> ORGANISM: Artificial Sequence
<220> FEATURE:
<223> OTHER INFORMATION: RTAP2 primer

<400> SEQUENCE: 9
actcactata gggctcgagc ggc                                             23

<210> SEQ ID NO 10
<211> LENGTH: 19
<212> TYPE: DNA
<213> ORGANISM: Artificial Sequence
<220> FEATURE:
<223> OTHER INFORMATION: HindIII

<400> SEQUENCE: 10
gtcgacggcc cgggctggt                                                  19

<210> SEQ ID NO 11
<211> LENGTH: 63
<212> TYPE: DNA
<213> ORGANISM: Artificial Sequence
<220> FEATURE:
<223> OTHER INFORMATION: BamHI SmaI - GUS

<400> SEQUENCE: 11
aagggcgaat tccagcacac tggcggccgt actagtggat ccccgggtgg tcagtccctt     60
atg                                                                   63
```